United States Patent
Ferguson et al.

(10) Patent No.: US 6,615,648 B1
(45) Date of Patent: Sep. 9, 2003

(54) ROAD PAVEMENT DETERIORATION INSPECTION SYSTEM

(75) Inventors: Ronald Allan Ferguson, Woodbine (AU); David Norman Pratt, Turramurra (AU); Paul Richard Turtle, Kirrawec (AU); Ian Barry Macintyre, Rosanna (AU); Daniel Peter Moore, Box Hill (AU); Patrick Dale Kearney, North Balwyn (AU); Michael John Best, Box Hill (AU); James Laurie Gardner, Thornleigh (AU); Mark Berman, Pymble (AU); Michael James Buckley, Pennant Hills (AU); Joseph Edmond Breen, Berowra Heights (AU); Ronald Jones, Wollstonecraft (AU)

(73) Assignees: The Roads and Traffic Authority on New South Wales (AU); Commonwealth Scientific and Industrial Research Organisation (AU)

( * ) Notice: Subject to any disclaimer, the term of this patent is extended or adjusted under 35 U.S.C. 154(b) by 0 days.

(21) Appl. No.: 09/582,306

(22) PCT Filed: Dec. 22, 1998

(86) PCT No.: PCT/AU98/01068

§ 371 (c)(1),
(2), (4) Date: Sep. 25, 2000

(87) PCT Pub. No.: WO99/32725

PCT Pub. Date: Jul. 1, 1999

(30) Foreign Application Priority Data

Dec. 22, 1997 (AU) ................................................ 991075

(51) Int. Cl.$^7$ .............................................. G01M 17/02
(52) U.S. Cl. ........................................ 73/146; 364/550
(58) Field of Search .............................. 75/146–146.8; 364/550, 557

(56) References Cited

U.S. PATENT DOCUMENTS

| 4,653,316 A | | 3/1987 | Fukuhara | |
| 4,899,296 A | * | 2/1990 | Khattak | ....................... 348/148 |
| 4,958,306 A | * | 9/1990 | Powell et al. | .................. 702/40 |
| 5,163,319 A | * | 11/1992 | Spies et al. | |
| D492,268 | * | 8/2000 | Hayashi | ..................... D16/202 |

FOREIGN PATENT DOCUMENTS

| FR | 2311141 A | 12/1976 |
| JP | 09-096515 | 4/1997 |
| JP | 09-101129 | 4/1997 |

* cited by examiner

*Primary Examiner*—Edward Lefkowitz
*Assistant Examiner*—Andre Allen
(74) *Attorney, Agent, or Firm*—Paul & Paul (57) ABSTRACT

A system for acquiring, processing, storing, analyzing and reporting data relating to the condition of a road or other pavement surface (102) in real time. The system includes a digital camera (104) mounted on a vehicle and positioned relative to a pavement surface (102) so as to capture images of the pavement surface (102) while the camera (104) is moving relative to the surface (102). The system also includes an illumination assembly (100) to illuminate the region from which an image is taken and an interface between the digital camera (104) and at least one computer. The system also includes a processor in the computer for processing the images to detect and classify cracks and other pavement surface (102) features.

42 Claims, 10 Drawing Sheets

Sample RoadCrack Database

| Chainage (km) | Roadloc Road# | Link | CW | Off | Chan | Temp | Frames | Wheel Path | Transverse Num | Transverse Ave Width | Longitudinal Num | Longitudinal Ave Width | Crocodile Num | Crocodile Ave Width | Non-Crack Features | Straight Features | Features |
|---|---|---|---|---|---|---|---|---|---|---|---|---|---|---|---|---|---|
| 0.100 | 00000373 | 0010 | A1 | 0.100 | 2 | 28 | 38 | L | 29 | 1.3 | 8 | 2.3 | 0 | 0.0 | 0 | 0 | Start of Test |
| 0.200 | 00000373 | 0010 | A1 | 0.200 | 2 | 28 | 40 | L | 19 | 1.2 | 7 | 2.2 | 0 | 0.0 | 0 | 0 | |
| 0.300 | 00000373 | 0010 | A1 | 0.300 | 2 | 28 | 40 | . | 0 | 0.0 | 0 | 0.0 | 0 | 0.0 | 0 | 0 | |
| 0.400 | 00000373 | 0010 | A1 | 0.400 | 2 | 28 | 40 | L | 9 | 1.5 | 0 | 0.0 | 0 | 0.0 | 0 | 0 | |
| 0.500 | 00000373 | 0010 | A1 | 0.500 | 2 | 28 | 40 | L | 5 | 2.5 | 0 | 0.0 | 0 | 0.0 | 0 | 0 | |
| 0.600 | 00000373 | 0010 | A1 | 0.600 | 2 | 28 | 40 | B | 8 | 2.8 | 0 | 0.0 | 0 | 0.0 | 0 | 0 | |
| 0.700 | 00000373 | 0010 | A1 | 0.700 | 2 | 28 | 40 | B | 8 | 3.1 | 0 | 0.0 | 0 | 0.0 | 0 | 0 | |
| 0.800 | 00000373 | 0010 | A1 | 0.800 | 2 | 28 | 40 | B | 14 | 2.6 | 0 | 0.0 | 4 | 1.1 | 0 | 0 | |
| 0.900 | 00000373 | 0010 | A1 | 0.900 | 2 | 29 | 40 | B | 10 | 2.1 | 0 | 0.0 | 0 | 0.0 | 0 | 0 | |
| 1.000 | 00000373 | 0010 | A1 | 1.000 | 2 | 29 | 40 | . | 0 | 0.0 | 0 | 0.0 | 0 | 0.0 | 0 | 0 | |
| 1.100 | 00000373 | 0010 | A1 | 1.100 | 2 | 29 | 40 | R | 0 | 0.0 | 0 | 0.0 | 0 | 0.0 | 0 | 0 | |
| 1.200 | 00000373 | 0010 | A1 | 1.200 | 2 | 29 | 40 | R | 0 | 0.0 | 14 | 1.3 | 0 | 0.0 | 0 | 0 | |
| 1.300 | 00000373 | 0010 | A1 | 1.300 | 2 | 29 | 40 | R | 0 | 0.0 | 9 | 1.2 | 0 | 0.0 | 0 | 0 | |
| 1.400 | 00000373 | 0010 | A1 | 1.400 | 2 | 29 | 40 | B | 0 | 0.0 | 2 | 1.9 | 0 | 0.0 | 0 | 0 | |
| 1.500 | 00000373 | 0010 | A1 | 1.500 | 2 | 29 | 40 | B | 0 | 0.0 | 23 | 1.8 | 0 | 0.0 | 0 | 0 | |
| 1.600 | 00000373 | 0010 | A1 | 1.600 | 2 | 29 | 40 | R | 0 | 0.0 | 22 | 2.0 | 0 | 0.0 | 0 | 0 | |
| 1.700 | 00000373 | 0010 | A1 | 1.700 | 2 | 28 | 40 | . | 0 | 0.0 | 16 | 1.7 | 0 | 0.0 | 0 | 0 | Change of Seal |
| 1.800 | 00000373 | 0010 | A1 | 1.800 | 2 | 28 | 40 | . | 0 | 0.0 | 0 | 0.0 | 0 | 0.0 | 0 | 0 | |
| 1.900 | 00000373 | 0010 | A1 | 1.900 | 2 | 27 | 40 | . | 0 | 0.0 | 0 | 0.0 | 0 | 0.0 | 0 | 0 | |
| 2.000 | 00000373 | 0010 | A1 | 2.000 | 2 | 27 | 40 | L | 0 | 0.0 | 11 | 1.1 | 17 | 1.7 | 0 | 0 | |

Fig. 10

ROAD PAVEMENT DETERIORATION INSPECTION SYSTEM

FIELD OF THE INVENTION

The present invention relates to a road pavement crack detection system and apparatuses associated therewith and more particularly relates to a crack detection system utilizing digital imaging for obtaining and storing data concerning the crack condition of a pavement.

BACKGROUND OF THE INVENTION

Cracking is the visible condition indicator most closely linked to pavement condition. Current methods do not detect cracking of the road network at the stage where early intervention would be cost effective nor attribute the incidence of cracking to a specific location (due to the small sampling). Major cost savings to authorities can be made from early intervention to seal finely cracked roads rather than waiting until the cracks develop to a more serious condition as is the case when using manual methods such as visual inspection. Finely cracked roads for instance can be sealed at a relatively low cost of $2–$4 per square meter on today's values compared to $30–$40 per square meter where cracking has progressed to a state requiring pavement rehabilitation.

There are a number of road crack measurement systems in use world wide. They range from passive systems such as video logging to active sensors such as lasers and ultrasonics. Feasibility studies have monitored the availability and performance of these technologies and commercially available systems. The existing systems are not capable of providing sufficient crack related data such as the ability to discern cracks on pavement surfaces including chip seal surfaces, at highway speeds. The existing systems further rely on post processing with manual intervention of image data in the office which often takes days before the data is available. Authorities have determined that there is a long felt want in this field of art to provide a system capable of delivering repeatable information on pavement cracking for common types of payment surfaces. As International Standards recommend that cracking is a major indicator of pavement condition, there is a need for an objective method for assessment of the extent of cracking on the road network. As a result, research has turned to automated crack detection systems but to date, and prior to the invention disclosed herein, to the best of the applicant's knowledge, no other trader or authority has arrived at a suitable automated system which delivers the level of results required to overcome known problems associated with present crack detection methodology. Many roads with low traffic volumes are economically designed to have a thin bituminous surface. Thin cracked surfaces are particularly vulnerable in wet weather when traffic pumps water into the road pavement leading to pavement failures which causes a roughening of the surface and decreased asset value of the roads. Pavement durability is preserved by sealing the surface well before extensive cracking appears.

Pavements such as roads, carriageways and the like are subject to heavy wear from traffic and degradation from sub-grade movement and deterioration in the pavement material itself. This necessitates regular monitoring of the pavement condition so the responsible government authority can plan maintenance programs and apply finances where it is most needed. This is a massive undertaking due to the usually extensive nature of road infrastructure. For efficient monitoring every increment of road surface must be studied across its full width in order to detect serious and also fine hairline cracks which have the potential to develop into more serious cracks posing dangers for road users. Although crack detection can be done visually by skilled personnel, it is almost impossible for visual inspections to obtain the necessary crack data for all sections of road in a particular municipality/region. The cost to do these inspections is prohibitive due to the amount of labour required and in any event such inspections suffer from the influence of human subjectivity and exposure to traffic hazards.

Another more sophisticated method of crack detection involves use of a video camera which films the road surface. The video image is then post processed to detect the severity and extent of cracking. A crack resolution of 3–5 mm is about the best that can be achieved in the prior art methods by using algorithms to do extrapolations from the data which is read.

Another method involves use of digital area scan cameras for achieving an image at high speed. The images from these cameras are prone to overlap and lack definition.

Pavement condition monitoring generally involves measurement of a roughness profile and assessment of parameters of pavement surface condition such as rutting, texture and cracking. Where cracks reach a certain size remedial surface treatments will not be an effective remedy so it is imperative that cracks are detected early and preferably when they are no larger than 1 mm.

The current manual methods of crack detection are time consuming and the extent of information gathered is limited. Manual methods are also capital intensive with poor return. There is clear need in the construction industry to arrive at more efficient ways of obtaining data concerning the condition of a pavement so that maintenance programs can be organized in the future and funds allocated.

OBJECT OF THE INVENTION

In order to overcome the shortcomings of the prior art methods the applicant determined that a survey vehicle could be equipped with automatic crack detection and classification systems using machine vision technology. This equipment would collect pavement condition data relating to cracking in conjunction with other equipment to measure road condition parameters such as roughness and rutting.

SUMMARY OF THE INVENTION

The present invention overcomes the shortcomings of the prior art by providing a crack detection system for accumulating and storage of data relative to the condition of a pavement. The invention further provides a system for obtaining digitized images of a pavement surface and computerized means for automatically analyzing the data thereby enabling efficient monitoring of the condition of the pavement surface. The present invention further provides a lighting assembly for use with a system for monitoring the condition of a road pavement surface wherein the lighting assembly enables illumination of fine pavement detail. The present invention further provides a digital camera for use with a system for monitoring the condition of a road pavement surface wherein the camera includes an automated exposure control enabling incremental snapshots of the pavement surface whilst the camera moves at up to and around 100 km per hour relative to the pavement. The invention further provides pavement monitoring software which stores, compiles and automatically assimilates data in "real time" relating to pavement condition obtained from a digital camera.

In broad terms, the system comprises a data acquisition vehicle having modular system equipment contained therein and which is capable of reading the condition of a pavement when the vehicle is travelling at speeds of up to 100 km per hour. Whilst 100 km per hour is considered an appropriate speed it will be appreciated that the system has been developed to accommodate faster speeds. Data from the data acquisition vehicle is obtained via the digital camera and is processed through an image processing pipe line which resolves the images into a condition enabling data on the road surface to be read. This data is then converted into computerized reports and can be compared with previously read data to provide a comparative analysis of the condition of a particular length of pavement.

In one broad form the present invention comprises a system for obtaining, storing, comparing and analyzing data relating to the condition of a pavement surface; the system comprising;

At least one digital image acquisition means positioned relative to a pavement surface so as to capture images of the surface whilst the digital image acquisition means is moving relative to the surface, an illumination assembly to illuminate the region from which an image is taken;

an interface between the digital image acquisition means and at least one computer processing means in said at least one computer for processing said images to detect and classify cracks and other pavement surface features.

In another broad form the present invention comprises the system as described above, including:

a lighting assembly for illuminating a pavement surface from which digitized images are taken for storage and analysis according to the process herein described, the assembly comprising;

a light source; and means for providing even intensity and direction of the light according to the level of exposure required by the digital image acquisition means.

In another broad form the present invention comprises the system as described above wherein the digital image acquisition means includes;

a digital camera;

said camera including a sensor, a time controlled automatic external electronic exposure which captures images of the pavement surface whether the camera is stationary or moving relative to the pavement surface and wherein the camera is responsive to reflectivity of the pavement surface.

According to a preferred embodiment, the pavement condition detection system is mounted on a vehicle allowing the digital image acquisition means to capture images of the pavement surface. The camera includes an interface for downloading images captured by the camera to a central processor which receives, stores, compares and analyzes data so as to provide via a user interface an up-to-date picture of the condition of the pavement.

In its broadest form the present invention comprises:

a system for real time capture and processing of pavement crack data comprising;

a vehicle capable of traveling at highway speeds;

means for capturing digital images of the pavement surface; and means for processing and displaying captured data.

Preferably, the digital image acquisition means comprises a digital camera and the processing means includes computer hardware and software for processing said digital images.

In its broadest form the present invention comprises:

a system for enabling real time capture and processing of data relating to the condition of a pavement the system comprising;

a vehicle capable of traveling at highway speeds;

means in or on said vehicle for capturing pavement crack data and means for processing and storage of captured data.

Preferably, the pavement is a road surface and said means for processing and storage of captured data includes means for removal of unwanted data.

In another broad form the present invention comprises;

a system for real time capture of and processing of pavement crack data relating to the condition of a road pavement said system comprising;

a vehicle capable of travelling at highway speeds;

a digital image acquisition means for capturing images of said pavement whilst said vehicle is in motion;

processing means for receiving and anaylsing data captured by said camera and for removal of any unwanted captured data.

There are a number of attendant benefits which attach to the system according to the present invention and these include reduced risk of injury to data collection personnel, less diversion of local resources to manual data collection, reduced time losses, eliminating inconsistencies in manually collected data, confidence in comparisons from year to year and region to region, confidence in accuracy of base data used for planning and budgeting, rational basis for use of cracking data in network performance, reporting and maintenance planning, reduced time at corporate level, collating data for reporting and planning, savings over current manual data collection and savings in cost of maintenance and rehabilitation of road network.

BRIEF DESCRIPTION OF THE DRAWINGS

The present invention will now be described in more detail according to preferred but non limiting embodiments and with reference to each form of invention and with reference to the accompanying drawings wherein.

DETAILED DESCRIPTION OF PREFERRED AND ALTERNATIVE EMBODIMENTS OF THE INVENTION

The present invention provides a modular automated system for crack detection in a pavement and more particularly detects finely cracked roads so that early repairs can be made to raise the overall condition of the road network. The automated crack detection system is contained in a vehicle which might be a truck or the like which is configured to enable all integers of the system to be contained within the vehicle. The parameters of the chosen vehicle are determined according to the operating requirements of the system. At the very least, the vehicle must have electrical mains power mainly for illumination, an ability to scan a predetermined width of pavement along with data capture systems to receive and process data captured by the automated crack detection system. Most of the electrical power is required for lighting so that a power generator located on the vehicle will be sized according to the power requirements per module. Other vehicle parameters include specified clearances between detection modules, internal space requirements for equipment, access for cabling and conduiting and a special configuration to suit user requirements. Each detection module of the preferred embodiment is designed to record crack data from a road imprint up to 750 mm wide and continuous in length in the direction of the vehicle motion. It is preferable that the conventional 25 meter truck width be maintained.

Figure 1:
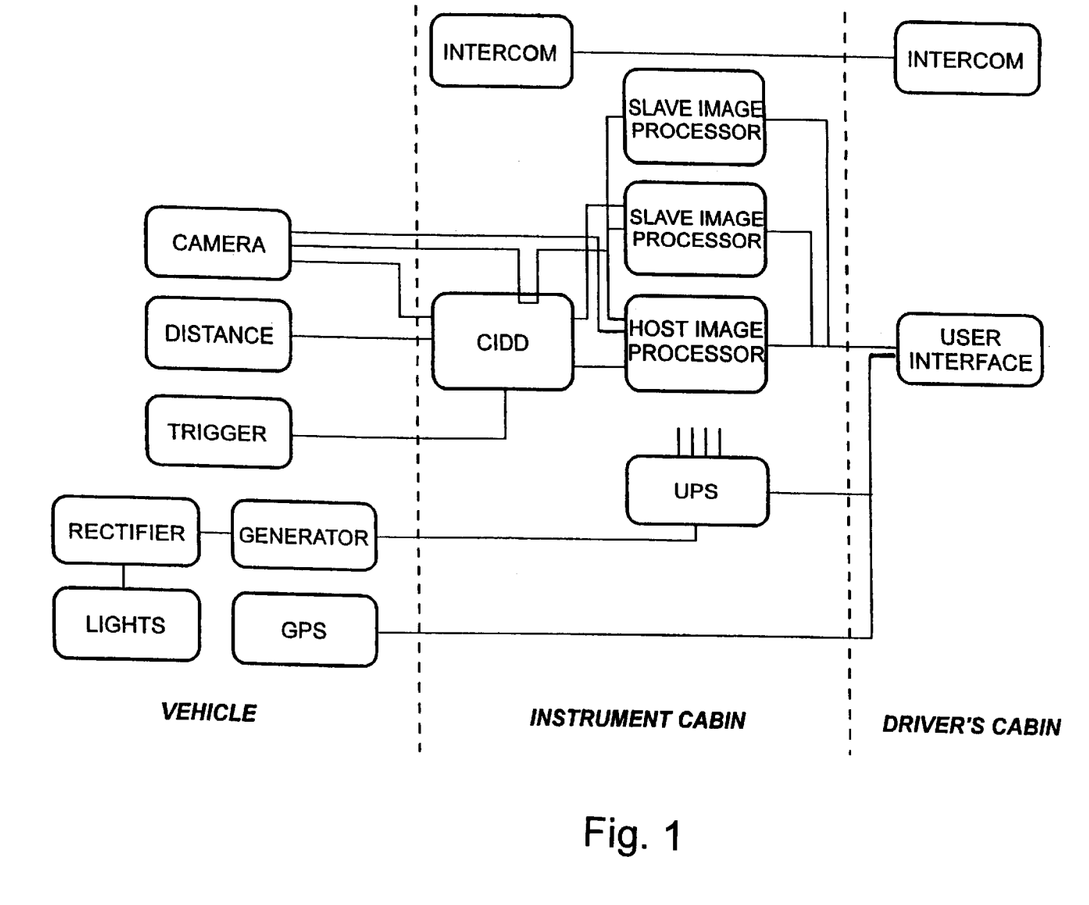
FIG. 1: shows a general schematic layout of the arrangement of the system aspect of the present invention.

Referring to FIG. 1 there is shown a schematic arrangement of an instrument configuration for the road crack truck. The instrument configuration is arranged into three areas, namely the vehicle, instrument cabin and driver's cabin. The key parts of this arrangement for implementation of the system are the vehicle and instrument cabin. Interaction between the vehicle hardware and software in the instrument cabin will be described in detail later.

As can be seen from FIG. 1 the vehicle includes integral hardware being a camera set at a predetermined distance from a road pavement surface, a trigger means, means for generating power and lights for illumination of the surface to be imaged.

In broad terms according to the system aspect of the invention there is provided a vehicle which is equipped with;

an image acquisition module which includes, a digital camera and illumination assembly.

The data captured by the camera is transferred into processing computers by means of a camera interface data distributor (CIDD). The data transferred to the computers is then processed by image processing software.

IMAGE ACQUISITION MODULE (1) CAMERA

The image acquisition camera includes a linear array sensor (which could include a photodiode, charge coupled device (CCD) or time delay integration (TDI) array of photosensitive elements) integrated into a camera. The sensor array is aligned transverse to the vehicle direction of travel. Camera, timing circuitry and an optical system are integrated with the sensor to record a millimeter of roadway per mm movement of the vehicle longitudinally. The number of light sensitive elements (pixels) in the linear array can be selected depending on the width of roadway to be inspected with a module (a number of image acquisition modules can be placed together to record large widths across a roadway). A 1024×1 pixel array was implemented in the prototype camera. The centre 750 pixels were used to create a 750 mm width image of the roadway per module. The rate at which the pixels can be read from the sensor has to be high (in the order of 40 Mhz) to allow images to be recorded at high vehicle speeds (up to 105 km/hr which equates to a line rate of up to approximately 29,000 lines per second. The sensitivity and quantum efficiency of the sensor was selected to provide sufficient charge output above noise, but below saturation exposure, for a given exposure (light intensity× integration time) to the light reflecting from various types of road surfaces. Typical road reflectance was 4–30%. To minimize blooming effects within the sensor from exposure saturation, caused by highly reflective quartz particles in the pavement surface, for example, it was necessary to incorporate anti-blooming circuitry. In addition, to minimize image blur at high vehicle speeds it was necessary to incorporate relatively short charge integration time capability (in the order of 1–20 microseconds) within the sensor. It was particularly important to maintain good image signal to noise characteristics at these sensor charge integration times. The correct exposure level was maintained by either varying the integration time and or varying the position of an 8 bit quantisation window within the 10 bit analogue to digital sampling of the sensor charge output. This exposure control methodology was based on digitally sensing the reflectivity of the binder materials in aggregate road surfaces. The exposure was adjusted to yield consistent crack contrast from the surrounding binder material, independent of what aggregate material (eg river gravel or blue-stone chip) is present. Set camera lens apertures were used. A depth-of-field of the camera lens must be greater than the vertical movement due to the suspension of the vehicle is necessary if road features are to remain in focus. Typically, a lens aperture of transmission equal to 50% of full aperture was used. This provided a depth-of-field greater than 300 mm for a camera placed approximately 600 mm above the roadway.

(2) ILLUMINATION

In order to obtain digitized images of the pavement surface with high integrity, it was found important to pay particular attention to the illumination of that surface. Contrast between the crack and road surface was maintained and illumination configuration was set to remove any unplanned shadowing which could interfere with machine/computer interpretation of the image. Accordingly, the field of view of the camera is preferably illuminated evenly across the whole field. To achieve this, a cylindrical reflector was used to focus linear quartz iodine lamps on the road surface. This ensured an appropriate level of illumination for adequate exposure of the line scan array. The design of the preferred embodiment provided even illumination across the linear array. In addition, the strip of focussed light provides a sufficient width of even illumination in the direction of the vehicle motion. This ensured the illumination strip did not move out of the camera's field-of-view as the vehicle moved up and down whilst travelling along the roadway, for example a focussed illumination beam strip of 900 mm by 30 mm was sufficient for a linear sensor field-of-view of the roadway of 750 mm. Cylindrical reflectors and lamps were placed before and after the camera relative to the truck direction. The angle that the illumination falls on the road surface is critical. It is possible that shadows can be mistaken for crack data. To prevent this, the position of the lamps has been set to maximize crack contrast and minimize shadows cast from textured road surfaces.

Figure 2:
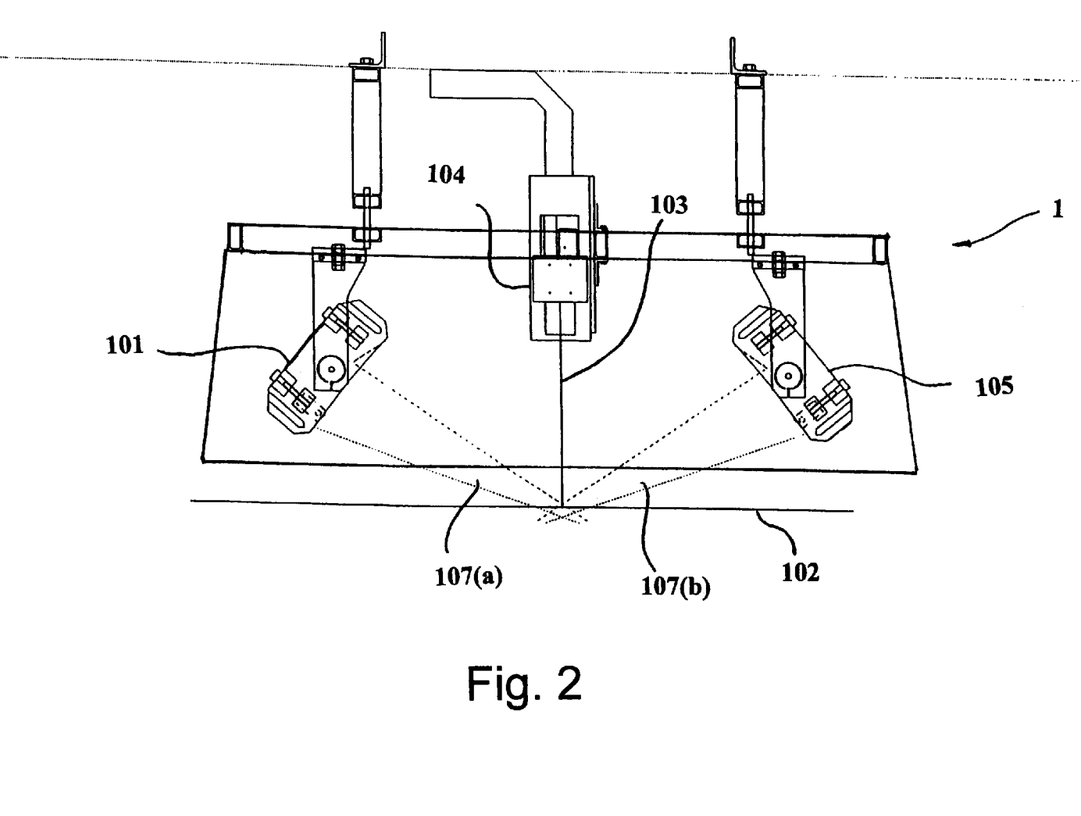
FIG. 2: shows an illumination module reflector placed with respect to a camera and roadway from different views.

FIGS. 2(a) and (b) show alternative views of an illumination assembly with respect to a camera and roadway. Referring to FIGS. 2(a) and (b) there is shown an illumination module 100 which includes reflectors 101 and 105 directed so as to illuminate a field of view on pavement surface 102 relating to the line of sight of 103 of camera 104. Dotted lines 107(a) and 107(b) represent the focussed illumination beam strip directed by reflectors 101 and 105 respectively onto pavement surface 102. In normal operation it is preferable that there be minimal movement between illumination beams relative to the camera axis. Such movement might be caused by vehicle vibration and vertical vehicle movement. The object in providing specific focussing for the lamps with cylindrical reflectors is primarily to ensure adequate levels of illumination on the road surface and, secondly, to ensure that the level of illumination remains evenly distributed transversely and longitudinally with respect to the camera's optical axis, even when there is relative movement between the camera's field of view and the focussed illumination strips on the roadway. However, image processing software has been implemented to address and correct for uneven illumination.

Figure 3:
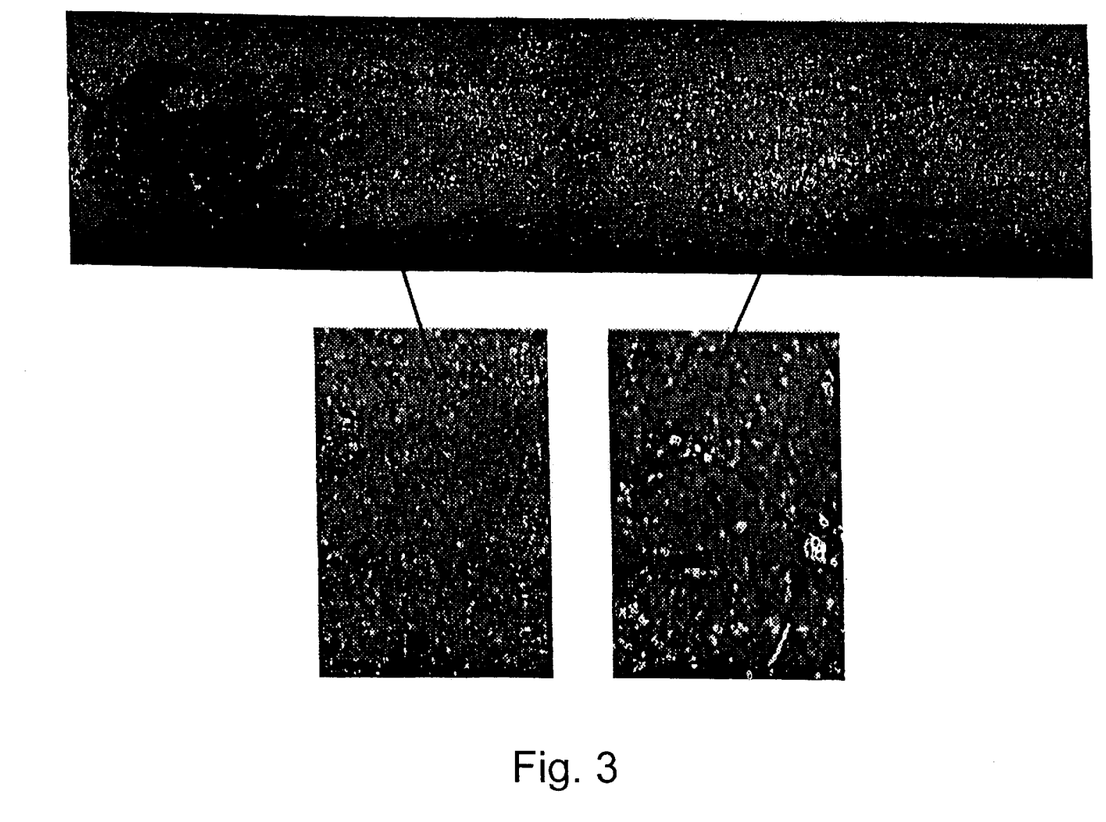
FIG. 3: shows an example of image processing sequence of a spray seal road surface acquired during trials.

In the preferred embodiment of the present invention, the interaction between the lighting exposure control and image capture is important for the proper functioning of the system. The exposure control of the preferred embodiment is regulated by means of appropriate software architecture. Tests have shown that exposure times as short as 1.0 micro seconds are now possible with a specially adapted sensor whereas previously exposure times no less than 10 micro seconds were possible. At high speeds, where exposure times were no shorter than 10 micro seconds, image blur occurred effecting the quality of the road data captured. The operation of the sensor in conjunction with the image acquisition module and based on the available illumination has shown that images of 1 mm cracks can be obtained. In field trials the performance of the image acquisition module was evaluated by recording road images from six trial reference sites. These sites were selected for the variation in road surface types and the type, severity and extent of road cracking. 15,000 trial images were recorded with a typical example depicting the image quality as shown in FIG. 3. FIG. 3 shows an example of an image on a spray seal road surface acquired during trials.

According to the apparatus aspect the electronic exposure control of the digital camera is able to change exposure time for different road surfaces. For dark roads it is possible with appropriate exposure time to obtain good contrast between the road binder and cracks.

(3) CAMERA INTERFACE DATA DISTRIBUTOR

The line scan camera employed in the preferred embodiment allows high speed operation with good dynamic range and accurate exposure control but requires more elaborate interfacing than does a conventional area camera. The computing power necessary for real-time processing of the road images greatly exceeds the capacity of a single CPU, so several computers must be used to provide the level of performance required for the RoadCrack system. The image data must be appropriately formatted and directed to a processor when computing resources become available on completion of a previous operation. The Camera Interface Data Distributor (CIDD) board combines the functions of camera control and data distribution.

The CIDD board performs several key functions in the system of the present invention, as follows:

1. Measurement of vehicle speed using signals from a rotary quadrature encoder mounted on a wheel hub
2. Setting of the control parameters for the camera software.
3. Generation of a control signal to initiate a read of one line of image data from the camera for each millimeter of vehicle motion. This is termed the START signal.
4. Generation of a control signal to allow the camera to integrate the electrical response to image intensity for a specified time. This implements an electronic exposure system which allows very precise control of image data dynamic range. This signal is denoted by the label SHUT.
5. Provide appropriate signals to allow synchronization of multiple image acquisition/processing units to ensure identical sampling patterns in all sampled paths.
6. Formatting of the camera data into frames of a size suitable for image processing.
7. Marking each such frame with a unique identification code.
8. Selection of frames for processing through use of a sampling table.
9. Distribution of frame data to the various image processing computers.
10. Monitoring of optical sensors to determine exposure parameters and verify correct system operation.
11. Generation and transmission to the host computer of a stream of data packets, each recording all important information relating to a particular image data frame.
12. Generation of a data stream to allow display of information on a LCD panel to assist the vehicle driver in maintaining the survey speed within the optimum range.

The CIDD board consists of a main printed circuit board and a daughter-board with a CPU. The main board carries the connectors required to interconnect the camera and the three frame-grabbers used to feed data into the image processing computers. RS422 standard differential receiver chips accept two parallel 10-bit data streams from the camera. The low, middle or high 8-bits of the 10-bit data may be selected for processing. The desired 8-bit data is packed into a 16-bit wide path, re-synchronized and transmitted in three identical streams using RS422 differential drivers. The daughter board carries a microprocessor which controls the CIDD operation, 1 Mbyte of static memory, an optional 1 Mbyte of ROM and a quad UART for serial communications support.

Communications between the CIDD board and host image processor is performed over a RS232 serial line using a packet-based command protocol. The microprocessor on the daughter board runs a small multi-threaded operating system to allow it to perform its various functions efficiently and not limit the rate of data throughput of the complete system. The CIDD software is written in assembly language to maximize performance. An overview of the CIDD software is presented below.

The operating system kernel supports multi-threaded operation using a simple scheduler. The scheduler allocates time-slices of 1/512 second and is invoked using an interrupt from the CPU periodic interval timer (PIT). A priority scheme is used to select the next task to be executed. A task may be suspended, if required, until a specific condition occurs. A thread may release the remainder of a time-slice if it cannot continue for any reason. Communications between threads is based on a simple event notification protocol. Shared resources are protected using semaphores whenever there is any potential for access conflict.

The various threads are as follows:

1. Each incoming command from the host computer is stored in a dynamically allocated packet buffer using a interrupt handler. The packets are stored in a queue for processing. The feed task maintains a reserve to two packet buffers for use by the handler since it is not possible to perform the memory allocation within an interrupt.
2. The execpacket task performs the action 'specified by each command packet. A response packet, if required, is placed in an output queue. The command packet is then modified to form an acknowledgment packet and placed in the output queue. In addition, it transfers frame data packets 3. The sendpacket task writes packets in the output buffer out over a serial line to the host computer.
4. Three tasks readport, writeport, and reportevent perform a similar function to the packet-based communications system, but are text-based to allow convenient software debugging over a serial port connection.
5. The camera$_{13}$ mon task manages the setting and verification of the camera software control parameters. It executes only at system initialization or when a change to some parameter is required.
6. The display_mon task maintains a display of important information on a LCD display for use by the survey vehicle driver.
7. The exposure$_{13}$ mon task monitors the output of the exposure sensor and computes the electronic exposure interval best suited to the road surface characteristics.
8. The status$_{13}$ mon task provides automatic control of the illumination 'system to prevent road damage due to overheating when the vehicle stops. It also checks for and reports abnormal conditions such as lamp failure.

The time-critical functions relating to camera timing, frame formatting and data distribution are performed using interrupt handlers and the Time Processor Unit (TPU) within the microprocessor. The TPU consists of a block of configurable I/O logic, memory and an embedded CPU which are organized to provide a wide variety of time-dependent I/O operations on up to 16 channels. The usage of the TPU for the CIDD board is described below.

Channel 5 is used to produce the START pulse for the camera, which initiates a readout of one image line. The TPU Synchronized Pulse Width Modulation (SPWM) function is used. The pulse period is controlled to give one line per millimeter of vehicle motion. This channel is used as the primary synchronization source for much of the CIDD operation.

Channel 6 uses the SPWM function to generate the SHUT signal. The electronic exposure interval may be adjusted from zero to any required value in approximately 240 nanosecond (ns) steps.

Channels 0, 1 and 2 are configured to produce a frame trigger pulse just before the start of a new frame. The pulse may be directed out of any one combination of the three channels. This pulse signals the frame grabber that the following frame should be saved and processed.

A distribution table of up to 512 entries is used to control the frame sampling strategy. Each table location of 8-bits specifies a required action. A pointer to the current table entry is incremented after each frame and reset back to the start after the last entry is reached. Bits 0, 1 and 2 indicate the frame should be saved by frame grabber 0, 1 or 2. Bit 7, if set, forces a reset of the access pointer. Bit 6 may be used to halt frame distribution after that entry is processed. This distribution method allows complete flexibility in the choice of sampling strategy.

Channel 3 issues an interrupt at the start of the first line in a frame. The interrupt handler then writes any required information for the last frame in a packet buffer and places that buffer in a queue for output by the execpacket task.

Channel 4 issues an interrupt at the start of the last line of a frame. The interrupt handler computes the average vehicle speed over that frame and updates the START period.

Channel 11 issues an interrupt which triggers generation of pulses on channels 0–2 at the appropriate time.

Channels 14 and 15 decode the quadrature signals from the rotary encoder to give an accurate estimate of vehicle motion.

Channels 12 and 13 are used to synthesize quadrature signals, similar to those from a rotary encoder, and are intended for diagnostic purposes.

Channel 10 is used to support interrupt mode RTS/CTS serial flow control over the internal MC68F333 serial interface.

Channel 7 receives input from both an optical sensor and a user-operated switch. Either input may initiate acquisition of camera data at the beginning of a survey, or introduce a reference mark in the packet communications data stream.

Channels 8 and 9 are used to support synchronization of multiple CIDD units.

Optimum control of the camera electronic exposure is facilitated through the use of a separate light sensor system. The system comprises a sensor with a spectral response matching that of the camera. A lens is used to allow the sensor to sample light reflected from the region of road surface viewed by the camera. The raw sensor signal is amplified, filtered and transmitted to the CIDD board where a combination of analog and digital techniques are used to compute the optimum exposure interval for the observed road characteristics.

The CIDD hardware and software can support reliable image acquisition at vehicle speeds from 4 to 105 km/hr when the image scale is such that one pixel corresponds to one millimeter on the road surface.

HOST AND IMAGE PROCESSING COMPUTERS

According to the system aspect of the invention there are ideally two ways of processing data obtained from the CIDD. The first of these is by way of a pipe line principle and the second by means of parallel distribution of data through processing computers. Software algorithms used in the processing of this data are the same irrespective of which of the two data processing systems are adopted.

According to one embodiment the hardware/software task functionality operates according to the following steps:

a) data is accepted from the digital camera;
b) framing signals are generated by the CIDD to form images for image processing;
c) image data is distributed to each of the image processing computers and to the host computer;
d) the host computer issues commands to set up the required functions for image processing and data generation.

The interaction of the hardware between obtaining road crack data and its storage assimilation and where applicable dilution is enabled by new software written specifically for the purpose. Operating system and software reside on a central hard disk attached to the host computer. The front end system and image processing units are diskless and boot from the host machine over an ethernet without user intervention. The front end system displays a user interface on a LCD screen/touch screen which allows the user to control the system remote from the host and processing computers. System software implemented includes:

a) control of system start up, initialization and control parameters;
b) communication with the camera interface and data distributor - interpretation of commands;
c) communication with the user interface computer— interpretation of commands;

d) user interface to set up, control and diagnose system instrumentation;
e) image and data acquisition and processing;
f) frame grabber control;
g) manage the distribution of image data processing load between parallel operating image processing computers;
h) apply the appropriate image processing algorithms to the image data;
i) merge frame information with processing results and generate output data file.

Figure 4:
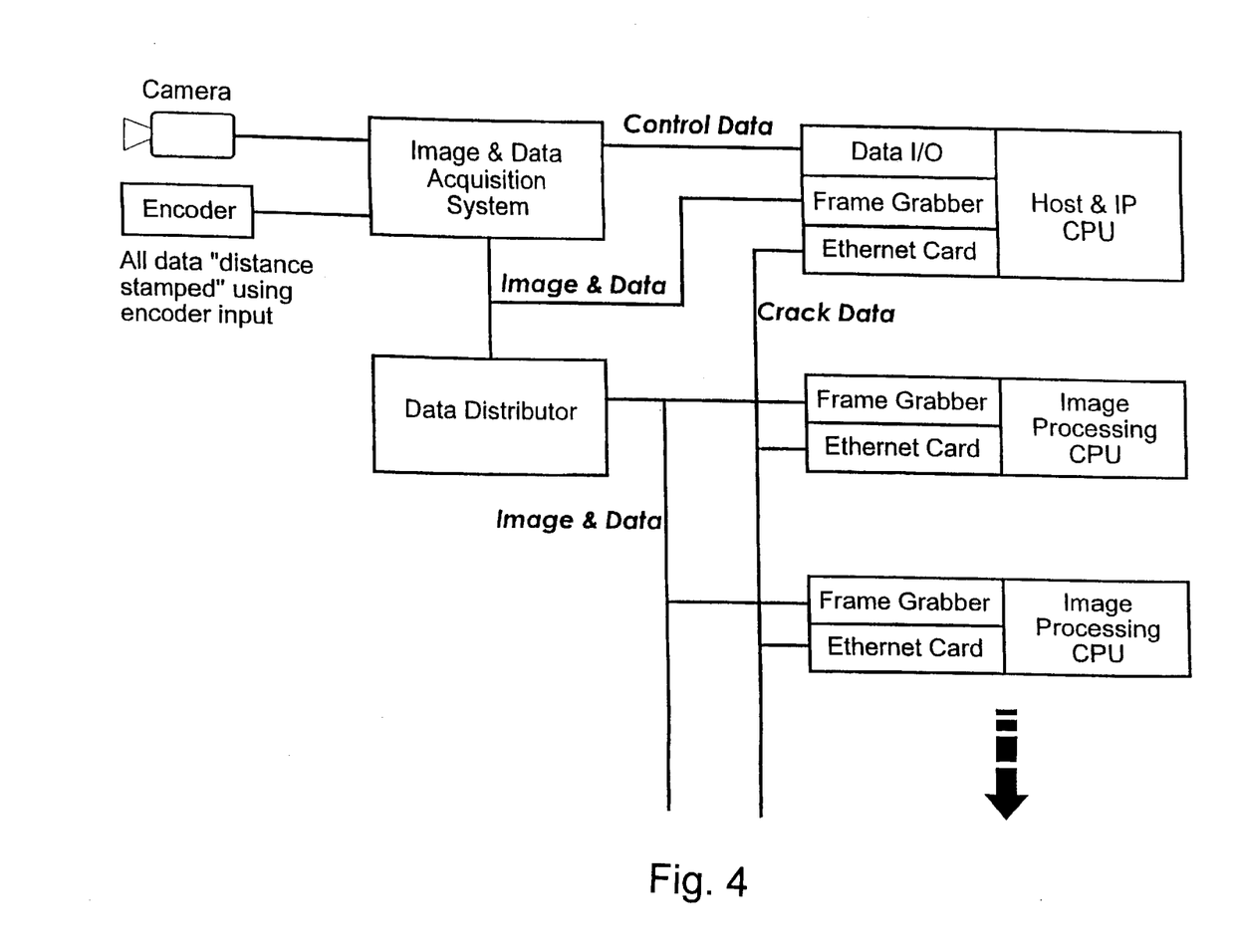
FIG. 4: shows a schematic layout of system hardware.
Figure 5:
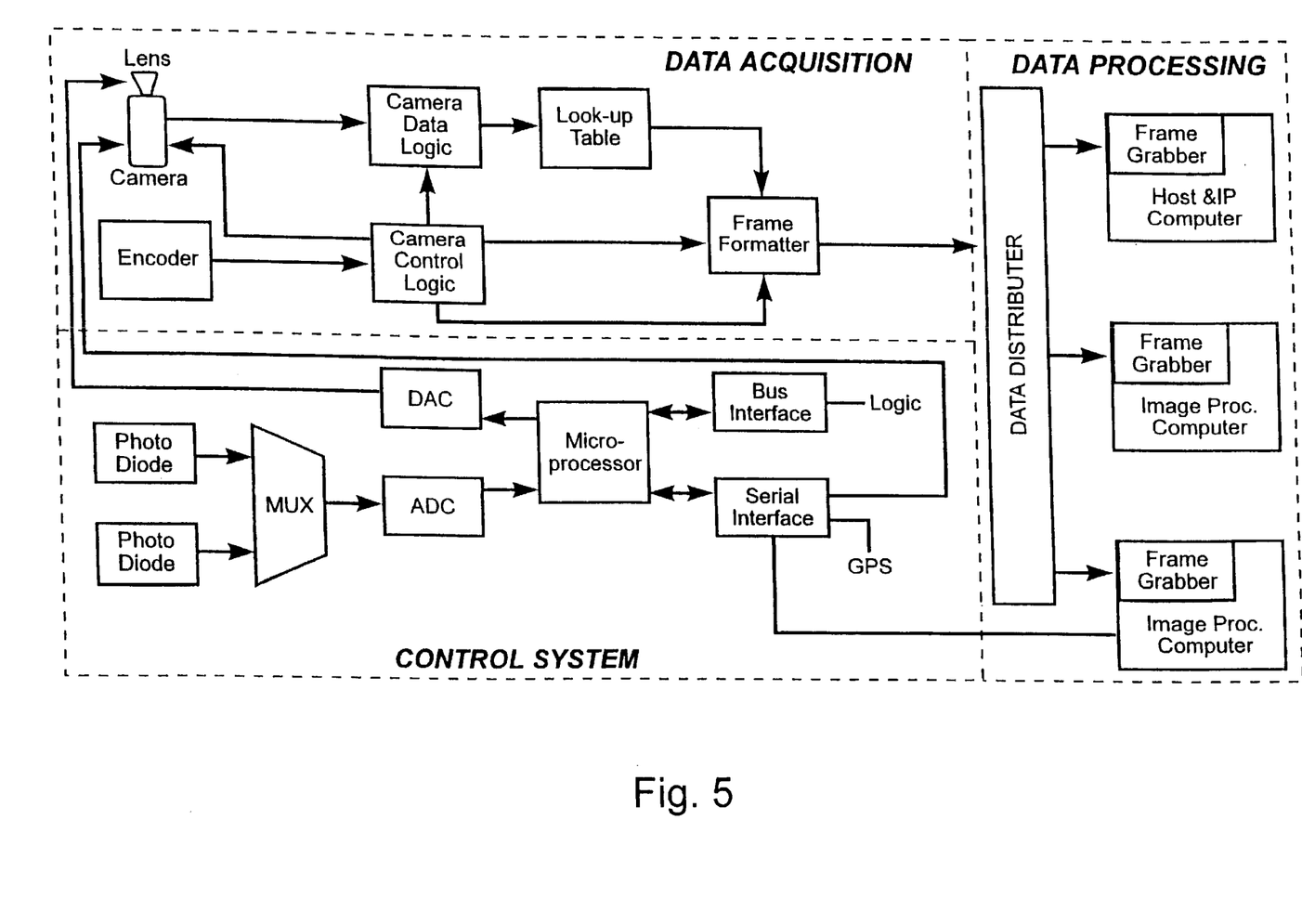
FIG. 5: shows a schematic layout of hardware including data acquisition, control system and data processing hardware.
Figure 6:
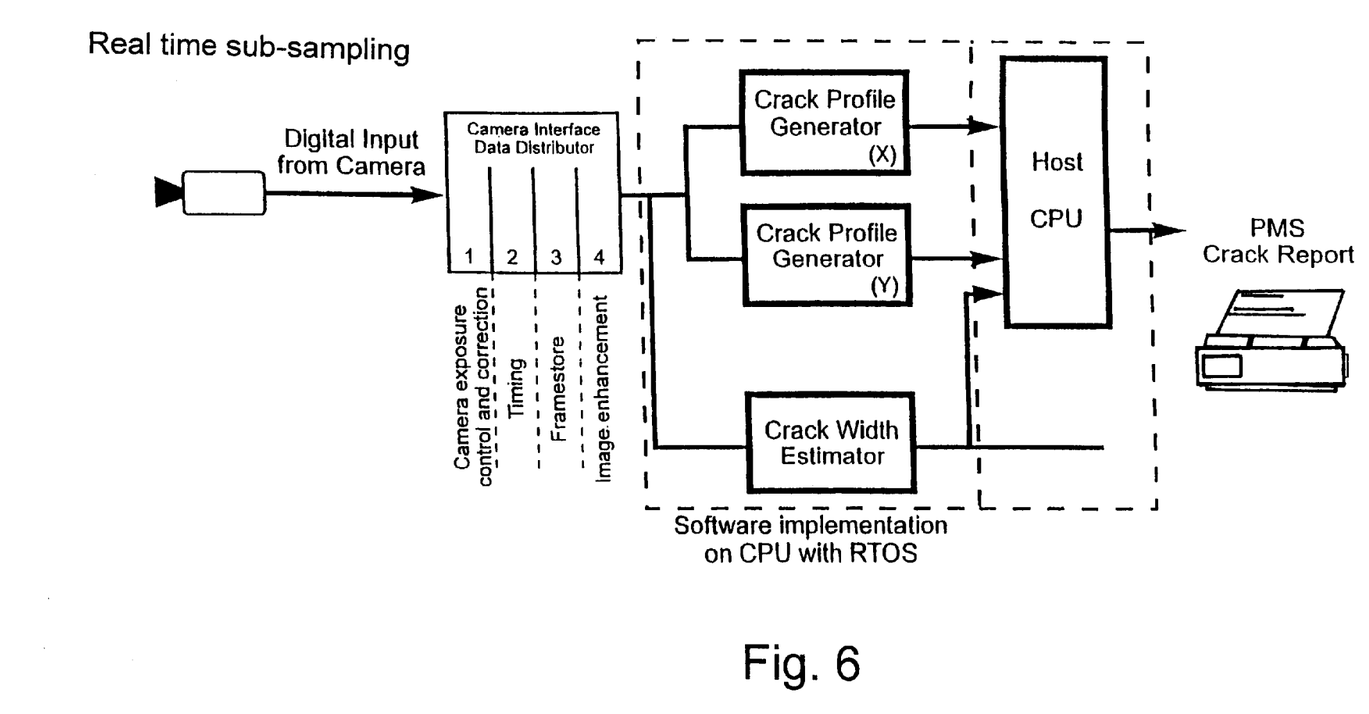
FIG. 6: shows a schematic layout of the system implementation (real time sub-sampling)
Figure 7:
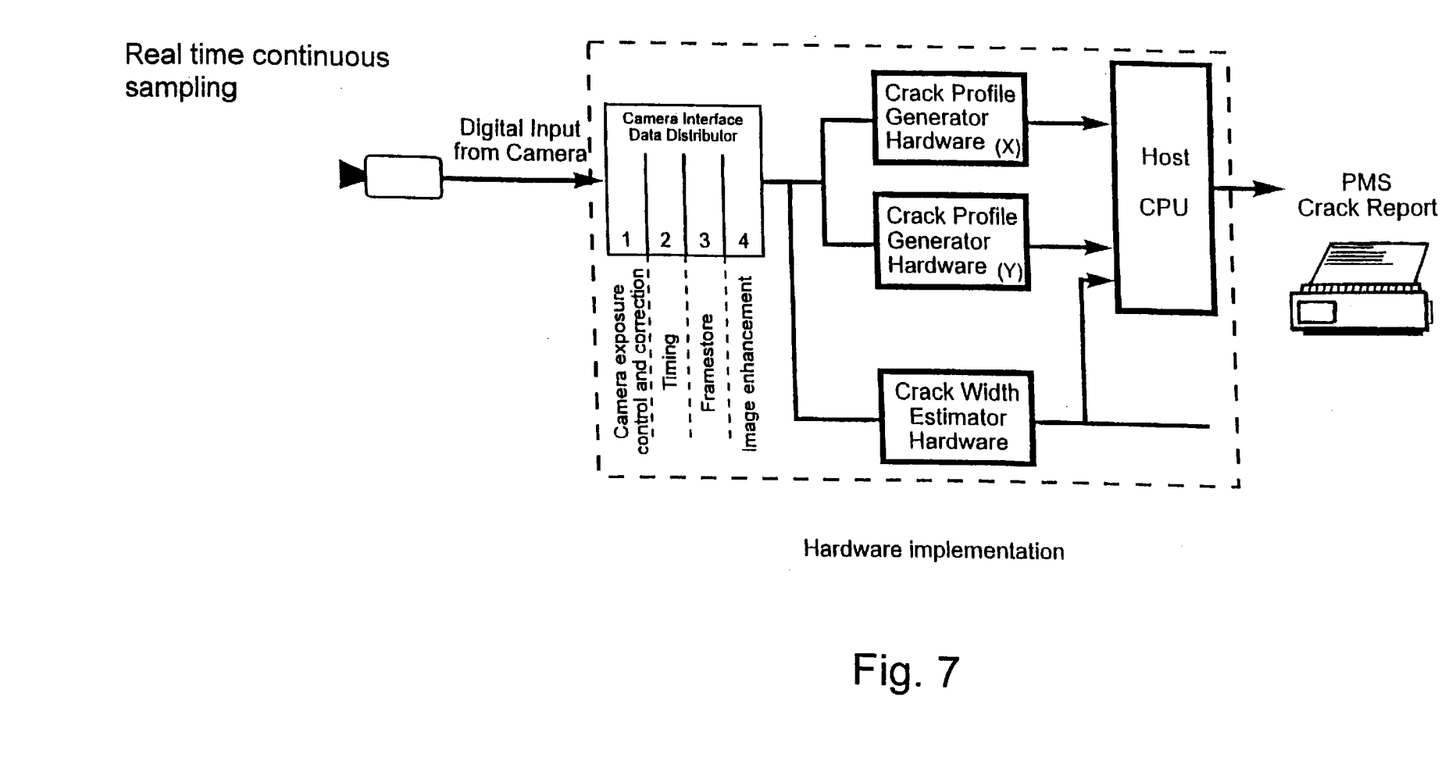
FIG. 7: shows a schematic layout of system implementation (real time continuous sampling long term)
Figure 9:
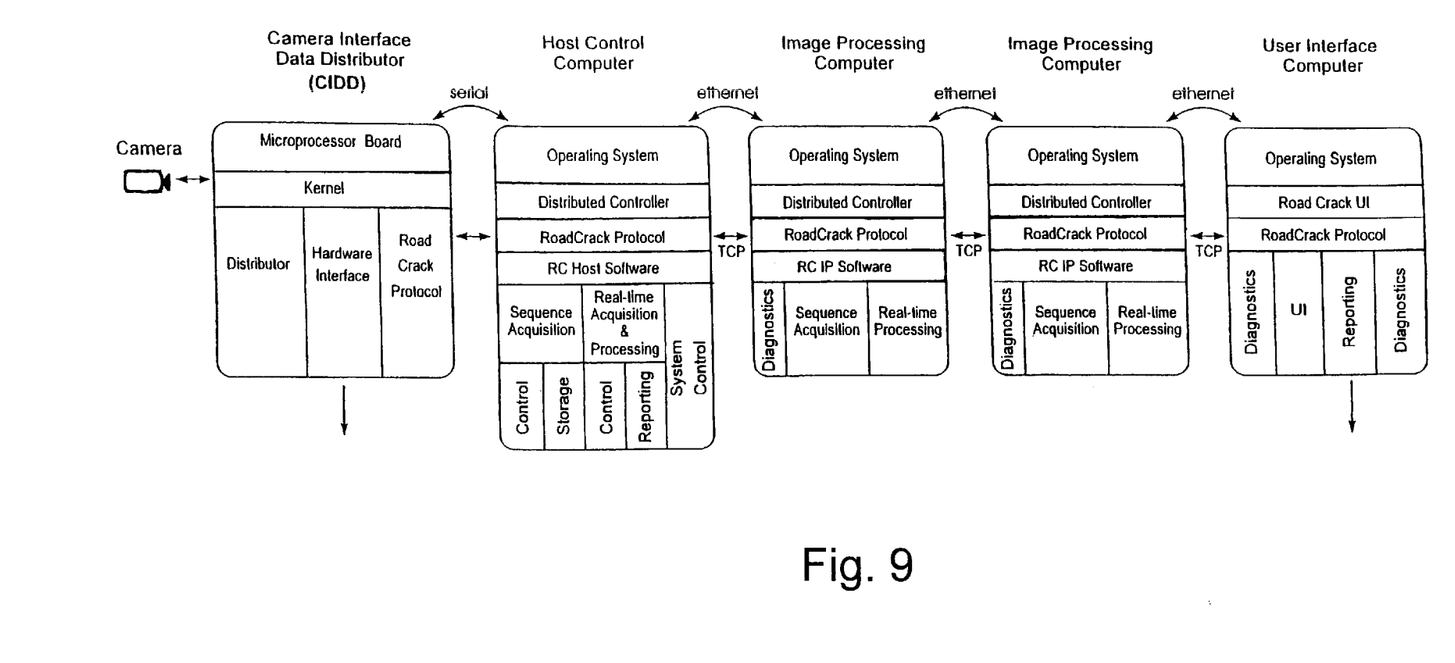
FIG. 9: Data logging sheet (raw data).

FIG. 4 shows a schematic layout of system hardware. FIG. 5 shows the hardware configuration categorized into data acquisition, control system and data processing. FIG. 6 shows a schematic layout of the software system implementation for real time sub-sampling. FIG. 7, shows a schematic layout of the software system implementation for real time continuous sampling. FIG. 9 shows a further general schematic layout of the arrangement of the system aspect of the present invention.

IMAGE PROCESSING SOFTWARE

The first step of the image processing algorithm uses a "separable rank filter" to filter the image. A binary image is produced in which a pixel is ON if its value in the original image is lower than the corresponding value in the filtered image.

In the second step candidates for longitudinal and transverse cracking are extracted using a shortest-path method. To find the candidate for longitudinal cracking, a longitudinal shortest-path is found through the binary image using a dynamic programming algorithm. This is the top-to-bottom path with the most ON values. From this path a contiguous segment of a certain fixed length is selected, again maximizing the number of ON values. This is the candidate segment of longitudinal cracking, and the number of ON values is the "longitudinal cracking score" for the image. A candidate segment of transverse cracking, and a "transverse cracking score" for the image are then computed in the same way using a left-to-right shortest path, except that a "transverse texture score" is also computed. Whereas the "transverse cracking score" is based on the maximum in the right-most column of the distance-to-left image, the "transverse texture score" is equal to the minimum in the right-most column of the distance-to-left image.

At each pixel on each candidate segment an integer crack width estimate is computed by inspecting the original image in the vicinity of the corresponding pixel. For each of the two candidate cracking segments, a smoothed median of these estimates is computed as the crack width estimate for the candidate segment.

The presence of longitudinal cracking is determined by comparing the "longitudinal cracking score" to a threshold.

The presence of transverse cracking is determined in a more complicated way:

If the "transverse cracking score" is above a threshold, then transverse cracking is determined to be present.

Otherwise, if the "transverse cracking score" is below another threshold, then transverse cracking is determined not to be present.

Otherwise, if the difference between the "transverse cracking score" and the "transverse texture score" exceeds a threshold, transverse cracking is determined to be present.

Otherwise, transverse cracking is determined not to be present.

If longitudinal cracking is detected, but transverse cracking is not detected, the cracking type is "longitudinal".

If transverse cracking is detected, but longitudinal cracking is not detected, the cracking type is "transverse".

If neither longitudinal nor transverse cracking is detected, the cracking type is "none".

If both longitudinal and transverse cracking are detected, or high density longitudinal cracking is detected, (see "Extent Measurement" below), the cracking type is "crocodile".

Extent Measurement

An algorithm exists for calculating the average number and extent of cracks in both the longitudinal and transverse directions within the image. Probable crack locations are identified by finding local maxima in the distance array which is an intermediate image in the shortest-path calculation. The results can be combined to estimate quantities such as density and extent of cracking in a frame.

If the extent of longitudinal cracking exceeds a threshold, then "high density longitudinal cracking" is detected.

Tyning Removal

Approximately transverse tyning is attenuated in the image used for transverse crack detection by use of a rank filter with a window one pixel high. When no tyning is present, the standard algorithm (described above) can be written:

$X1 = \text{transverse}_{13} \text{ rank}(X0, nx)$ $X2 = \text{longitudinal}_{13} \text{ rank}(X1, ny)$ $B2 = X0 < X2$ $\text{transverse}_{13} \text{ detect}(B2)$ $\text{longitudinal}_{13} \text{ detect}(B2)$ where X0 is the input image, and nx and ny are, respectively, the transverse and longitudinal dimensions of the filter.

When tyning removal is required the order is slightly altered so that transverse detection is carried out on an image which is produced by purely transverse filtering:

$X = \text{transverse}_{13} \text{ rank}(X0, nx)$ $B1 = X0 < X1$ $\text{transverse}_{13} \text{ detect}(B1)$ $X2 = \text{longitudinal}_{13} \text{ rank}(X1, ny)$ $B2 = X0 < X2$ $\text{longitudinal}_{13} \text{ detect}(B2)$

USER INTERFACE:

Operator access to the system during routine data collection activities is provided via a notebook computer, or "touch-screen" type device located in the front cabin of the host vehicle. The main functions of the user interface are:

system initialisation and control selection from a list of data collection modes initiation of data collection, in a selected mode of operation road location referencing and input of special features and events real-time processing of road cracking provided as operator feedback Operation of the RoadCrack equipment produces records of road pavement cracking information referenced against an accurate distance reference determined from a measurement transducer. Selection of an optional road location referencing system produces a scrolling list of roadside features which are synchronized with the distance measurement record. Provision is made for a location referencing system specific to the needs of the road authority. Recording of data for intervals of 10 m, or shorter, being less than the proposed 100 m reporting interval, allows data to be collected in each direction of a roadway to be consistently reported from a common referencing point.

The extent of operator intervention is minimized by provision of menu-prompts to minimize the subjectivity applied to the data collection process and thereby reduce the potential for error. System information is provided on the operating screen to allow direct operator response to extraordinary conditions encountered during the period of operation. The user interface provides operator feedback which includes an indication of the cracking determined from "real-time" processing. The provision of this information allows the operator to record or respond to any anomalies or problems which may corrupt the integrity of the data during the period of operation of the RoadCrack system. A summary report and data disk is provided at the end of each data collection run and no significant further processing is required to produce more detailed reporting formats.

DATA SUMMARISING AND REPORTING

The raw data format from the acquisition system consists of a number of individual record types each denoted by single letter prefixes. This data set contains information relating to Velocity, Exposure, Road Location Information, as well as Cracking summaries for each 500 mm×750 mm image frame collected by the system. For each 500 mm×750 mm image frame, the system reports the predominant cracking type (transverse, longitudinal, crocodile or none), the cracking severity and crack width along with various other values relating to the camera timing and processing parameters.

This frame centric data is then summarized by combining frames occurring within each 10 meter longitudinal segment into a single record. The method of summarizing the data centres around recording the numbers of records that fall into various categories. By recording the total number of image frames analyzed within the 10 meter segment, the number of frames recording each type of cracking can be reported as a percentage of the total images analyzed. This reporting method enables comparable results from successive surveys to occur, even if the number of modules, or sampling methods change over time.

When summarizing the data into 10 meter segments, the frames are first categorized by predominant crack type and by crack width. This becomes the intermediate Road Crack Data (RCD) format data file.

Figure 10:
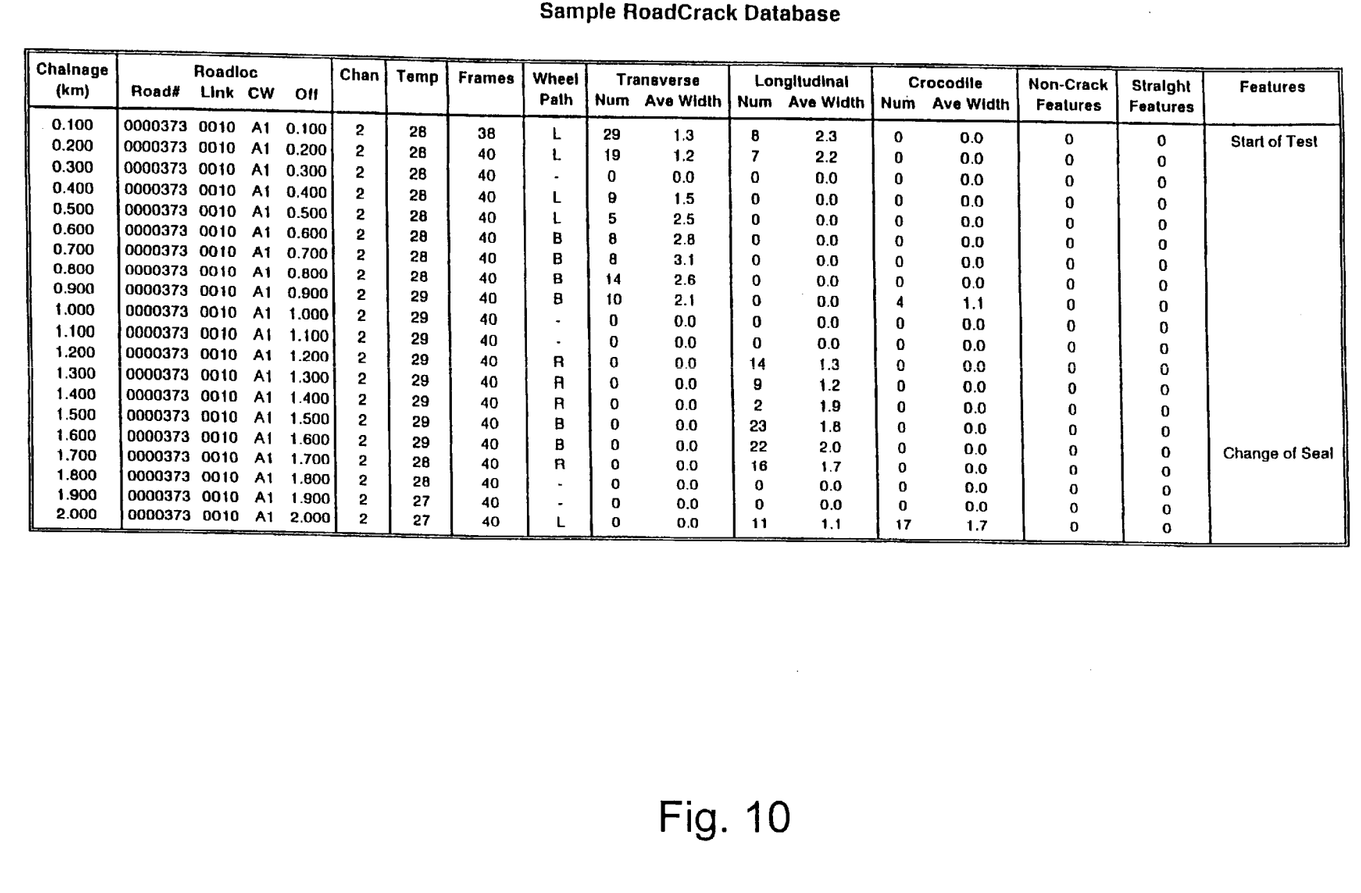
FIG. 10: Shows Road Condition Reports.

The final reporting step involves further summarizing the RCD file into 100 meter segments, as shown in FIG. 10. For each 100 meter segment, the total number of frames is reported. This is followed by detailed breakdowns of the number of frames exhibiting cracking in each of the three crack types along with the average crack widths for each. Road Location Data and/or miscellaneous features entered by the operator during acquisition are also reported in relation to the cracking data.

Figure 8:
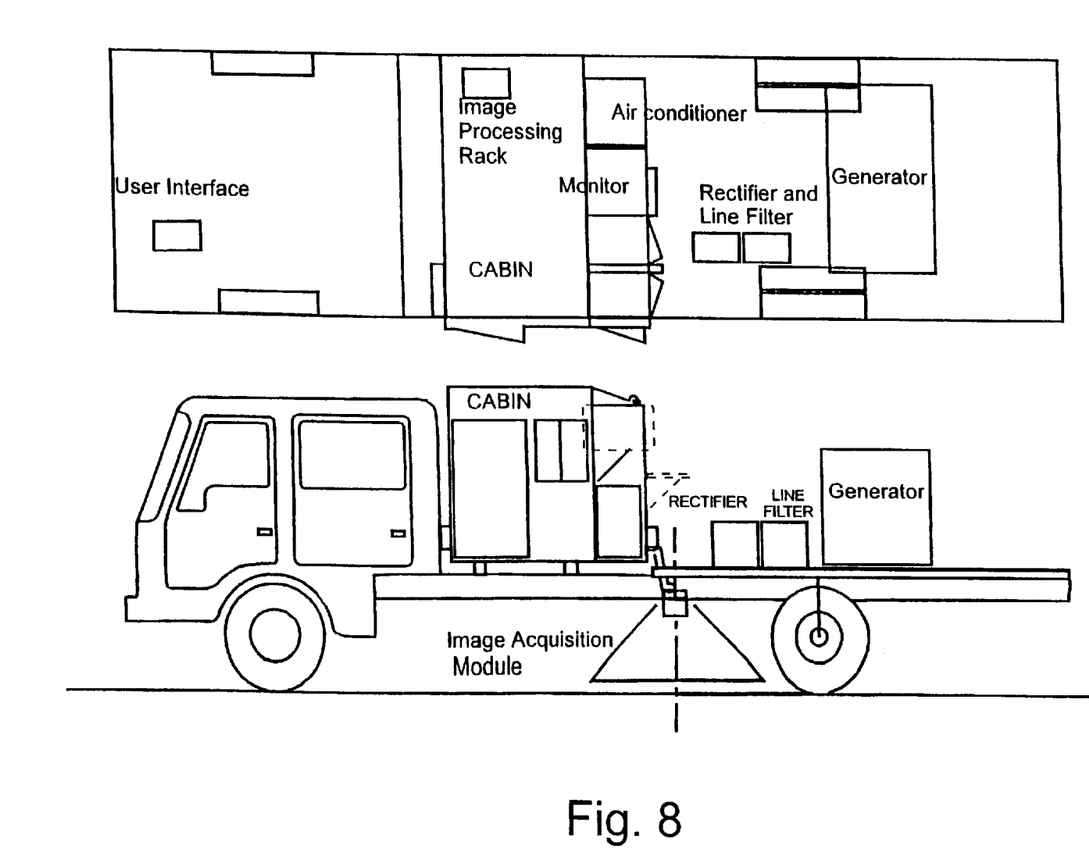
FIG. 8: shows a typical data acquisition vehicle showing a possible equipment layout.

FIG. 8 shows a side elevation and plan view of a vehicle showing an equipment layout according to one embodiment of the invention.

It will be recognized by persons skilled in the art that numerous variations and modifications may be made to the invention as broadly described herein without departing from the overall spirit and scope of the invention.

What is claimed is:

1. A system for acquiring, processing, storing, analyzing, and reporting data relating to the condition of a road or other pavement surface in real time; the system including; at least one digital image acquirer positioned relative to a pavement surface so as to capture images of the pavement surface while the digital image acquirer is moving relative to the pavement surface; and illumination assembly to illuminate the region on the pavement surface from which an image is taken; an interface between the image acquirer and at least one computer; a processor in said at least one computer for real time processing of said images to detect and classify cracks and other pavement surface features.

2. The system as claimed in claim 1 wherein said interface manages the manner in which the digital image acquirer acquires images.

3. The system as claimed in claim 2 wherein said interface adjusts the acquisition timing of the digital image acquirer in relation to the speed at which said digital image acquirer is moving relative to the pavement surface.

4. The system as claimed in claim 3 wherein said interface also adjusts the acquisition timing of the digital image acquirer relative to the reflectivity of the pavement surface.

5. The system as claimed in claim 4 wherein said digital image acquirer is capable of receiving at least one line of image data for every 1 millimeter of movement of said digital image acquirer relative to said pavement surface.

6. The system as claimed in any one of claims 2 to 5 wherein said interface includes a synchronizer for synchronizing the acquisition and processing of images from more than one digital image acquirer.

7. The system as claimed in claim 1 wherein said interface also manages the flow of data to said processor to enable real time processing of said data.

8. The system as claimed in claim 7 wherein said real time processing of said data includes real time continuous processing, real time continuous processing by subsampling, and storage of said data to allow real time post-processing at some later time.

9. The system as claimed in claim 8 wherein said interface manages the flow of data to said processor by a number of steps including:
   (a) formatting each acquired image to a size suitable for processing;
   (b) marking each image with a unique identification code; and
   (c) distributing the images to the processor.

10. The system as claimed in claim 9 including the additional step of selecting a subsample of acquired images for processing.

11. The system as claimed in claim 10 wherein said subsample is selected by means of a sampling table.

12. The system as claimed in claim 9 wherein said unique identification code contains information relating to the location at which the image was acquired.

13. The system as claimed in claim 12 wherein said information on the location at which the image was acquired is at least partly provided to said interface by means of a Global Positioning System (GPS) and/or a road location reference system.

14. The system as claimed in claim 1, wherein said processor is capable of analyzing images of at least one type of road surface in real time.

15. The system as claimed in claim 14 wherein said processor is capable of analyzing images of more than one type of pavement surface in real time.

16. The system as claimed in claim 15 wherein said types of pavement surface include:

i) sprayed seal;
ii) asphalt; and
iii) concrete.

17. The system as claimed in claim 14 wherein said processor processes said images to detect and classify cracks and other pavement surface features by performing a number of steps including:
  i) image filtering;
  ii) crack isolation; and/or
  iii) crack measurement.

18. The system as claimed in claim 14 wherein said processor utilizes a number of algorithms to detect and classify cracks and other pavement surface features including:
  i) a rank filter algorithm;
  ii) a shortest path algorithm;
  iii) a cracking score algorithm;
  iv) a texture adjustment algorithm; and/or
  v) a cracking density algorithm.

19. The system as claimed in claim 14 wherein said processor includes means for separating out artifacts and textures on the pavement surface.

20. The system as claimed in claim 19 wherein said means for separating out artifacts and textures on the pavement surface includes means for the removal of or compensation for tyning and blooming from the images.

21. The system as claimed in claim 14 wherein said processor classifies said cracks as:
  i) transverse cracks;
  ii) longitudinal cracks;
  iii) crocodile cracks; and/or
  iv) straight/non-cracked features.

22. The system as claimed in claim 14 wherein said processor includes either a pipeline processor or a parallel processor.

23. The system as claimed in claim 22 wherein said pipeline processor includes a series of circuit boards capable of analyzing said acquired image data continuously in real time.

24. The system as claimed in claim 22 wherein said parallel processor includes a plurality of image processing CPUs arranged in parallel, each processing a subsample of the acquired data in real time.

25. The system as claimed in claim 1 wherein said illumination assembly includes; a light source; and apparatus for controlling the intensity and direction of light according to the level of exposure required by said digital image acquirer.

26. The system as claimed in claim 25 wherein said apparatus for controlling the intensity and direction of light includes at least one reflector which concentrates the light emitted from the light source on an area of the pavement surface from which the digital image is taken.

27. The system as claimed in claim 26 wherein said reflector is a cylindrical reflector and said light source is a linear quartz iodine lamp.

28. The system as claimed in claim 1 wherein the digital image acquirer is a digital camera and includes a sensor; a time controlled automatic external electronic exposure which captures images of the pavement surface at a speed which is proportionate to the speed at which the digital image acquirer is moving relative to the pavement surface, and which takes the reflectivity of the pavement surface into account.

29. The system as claimed in claim 28 wherein said sensor includes any one of:
  a) a photodiode;
  b) a charged coupled device (CCD); or
  c) a time delay integration (TDI) of photosensitive elements.

30. The system as claimed in claim 1 wherein the system is mounted on a vehicle, allowing the digital image acquirer to capture images of the pavement surface as the vehicle moves along the pavement.

31. The system as claimed in claim 30 wherein said vehicle is capable of travelling at highway speeds.

32. The system as claimed in claim 31 wherein said highway speeds includes speeds between 5 kilometers per hour and 120 kilometers per hour.

33. The system as claimed in claim 30 wherein said information on the location at which the image was acquired is at least partly provided to said interface from information obtained from a distance transducer attached to a moving part of the vehicle.

34. A system for real time capture and processing of pavement crack data comprising; a vehicle capable of travelling at highway speeds, a digital image capturer mounted in or on said vehicle for capturing digital images of the pavement surface; and a processor in communication with said digital image capturer, the processor for processing at least part of said captured data in real time, wherein the processor in communication with said digital image capturer includes a digital camera and the processor means includes computer hardware and software for processing said digital images.

35. The system as claimed in claim 34 wherein said highway speeds includes speeds between 5 kilometers per hour and 120 kilometers per hour.

36. A system for enabling real time capture and processing of data relating to the condition of a pavement, the assembly including; a vehicle capable of travelling at highway speeds; a pavement crack data capturer mounted in or on said vehicle for capturing pavement crack data; and a processor for processing captured data in real time.

37. The system as claimed in claim 36 wherein the pavement is a sprayed seal, asphalt or concrete surface and said means for processing and storage of captured data includes means for removal of unwanted data.

38. The system as claimed in either of claims 36 or 37 wherein said highway speeds include speeds between 5 kilometers per hour and 120 kilometers per hour.

39. A system for real time capture of and processing of pavement crack data relating to the condition of a road pavement, said system comprising; a vehicle capable of traveling at highway speeds; a digital camera mounted in or on said vehicle for capturing images of said pavement while said vehicle is in motion; a processor mounted in or on said vehicle, and linked to said camera, for receiving data captured by said camera, and for removal of any unwanted captured data in real time.

40. The system as claimed in claim 39 wherein said highway speeds include speeds between 5 kilometers per hour and 120 kilometers per hour.

41. The system as claimed in claim 1 wherein data is stored in any one of the following ways:
  i) no images are saved and only detection and classification results are saved;
  ii) only images are saved;
  iii) both images and detection and classification results are saved; or iv) a sample of images and their corresponding detection and classification results are saved.

42. A method for real time capture and processing of pavement crack data comprising the steps of:

(a) using digital image acquirer having an electronic exposure control and positioned relative to a pavement surface to capture images of the surface while the digital image acquirer is moving relative to the surface, in conjunction with an illumination assembly which illuminates the region from which an image is taken;

(b) using an interface between the digital image acquirer and at least one computer to manage the manner in which the digital image acquirer acquires images and to manage the way in which the acquired data is passed on to an image processing CPU;

(c) using software and/or hardware in an image processing CPU to process said images(s) of the pavement loaded into the computer by a number of steps which include:
  i) image filtering;
  ii) crack isolation; and/or
  iii) crack measurement; and (d) processing the images in real time and providing real time reporting of pavement crack data.

* * * * *